United States Patent [19]

Bandurco et al.

[11] Patent Number: 5,240,953
[45] Date of Patent: Aug. 31, 1993

[54] SUBSTITUTED TRIAZOLES AS ANGIOTENSIN II INHIBITORS

[75] Inventors: Victor T. Bandurco, Bridgewater; William V. Murray, Belle Meade; Michael P. Wachter, Bloomsbury; Charles F. Schwender, Califon, all of N.J.

[73] Assignee: Ortho Pharmaceutical Corporation, Raritan, N.J.

[21] Appl. No.: 828,394

[22] Filed: Jan. 30, 1992

[51] Int. Cl.$^5$ ............... A61K 31/41; A61K 31/435; C07D 403/12; C07D 403/14
[52] U.S. Cl. .................. 514/381; 514/340; 514/383; 546/276; 548/252; 548/264.2; 548/264.4
[58] Field of Search ............... 548/252, 264.2, 264.4; 514/381, 383, 340; 546/276

[56] References Cited

U.S. PATENT DOCUMENTS 5,093,346 3/1992 Carini et al. ............... 548/252

Primary Examiner—Patricia L. Morris

[57] ABSTRACT

This invention relates to novel bis-biphenyl substituted 3-mercapto-1,2,4-tetrazoles and to pharmaceutically acceptable salts thereof.

The compounds are angiotensin II receptor antagonists, and are useful in treating hypertension (lowering high blood pressure), congestive heart failure, elevated ocular pressure, cerebral stroke, angina, cardiac insufficiency, myocardial infection or diabetic nephropathy.

The invention also relates to pharmaceutical composition comprising a compound of the invention, a method of treating a physiological condition in a mammal that is mediated by angiotensin II which comprises administering to the mammal an effective amount of a compound of the invention, and novel processes for preparing the compounds of the invention.

8 Claims, No Drawings

SUBSTITUTED TRIAZOLES AS ANGIOTENSIN II INHIBITORS

FIELD OF THE INVENTION

This invention relates to novel compounds of the following formulae:

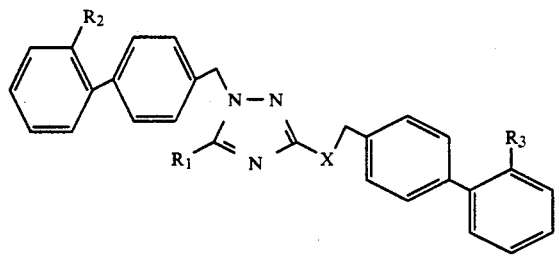

and

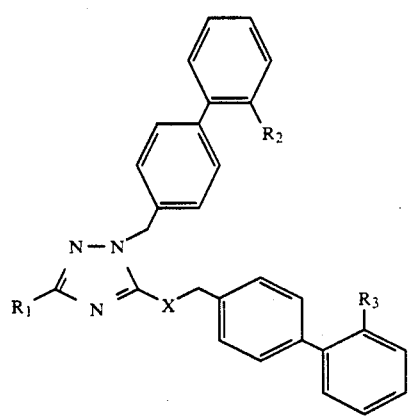

The invention also relates to pharmaceutical compositions comprising a compound of the invention as the active ingredient, a method of treating a physiological condition in mammals that is mediated by angiotensin II by administration of a compound of this invention, to novel processes for preparing the compounds of the invention and to pharmaceutically acceptable salts thereof.

The novel compounds are angiotensin II receptor antagonists and are useful in treating hypertension (lowering of high blood pressure), congestive heart failure, elevated ocular pressure, cerebral stroke, angina, cardiac insufficiency, myocardial infarction and diabetic nephropathy.

BACKGROUND OF THE INVENTION

The role of hypertension in cardiac dysfunction is continually evolving. Therefore, the treatment of hypertension continues to be clinically important. The discovery of new agents with fewer undesirable side effects is a therapeutic target since hypertension must be treated chronically. Long term toxicity as well as long term patient compliance are important considerations in the development of new antihypertensive agents.

One of the blood pressure regulating systems in man is the renin-angiotensin system. The renin-angiotensin system produces angiotensinogen in the kidney which is converted by renin to angiotensin I. The nonvasoconstricting peptide angiotensin I is converted by angiotensin converting enzyme (ACE) to angiotensin II, a potent vasoconstrictor. The discovery of nonpeptide angiotensin converting enzyme (ACE) inhibitors represented an important new step in the treatment of hypertension and several of these inhibitors, such as captopril and enalapril, are widely accepted. Progress toward renin inhibitors as therapeutic agents, however, has been far less successful.

Direct antagonism of angiotensin II binding at the receptor is an attractive goal because it is the actual vasoconstricting event in this pathway. By inhibiting the receptor, one would expect to have fewer side effects than by inhibiting earlier steps in the pathway. Also, by acting at the receptor, as opposed to ne of the enzymes, large deposits of angiotensinogen and angiotensin I should not build up. In some systems, this build up can give rise to shunting mechanisms which can lead to other side effects.

Duncia et al.[J. Med. Chem., (1990), 33, 1312] Carini et al.[J. Med. Chem. (1990), 33, 1330], Johnson et al.[Drug News and Perspectives, (1990), 3,(6), 337], Chang et al. (EP 041,594 A) and Roberts et al. (G.B. 18402) all describe compounds which are inhibitors of angiotensin II.

A number of 3-thio-1,2,4-triazoles have been described in the literature [Beyer, H. et al., Ber. (1960) 637, 135; Kroger, C. et al., Ber (1961) 643, 121; and Kroger, C. et al., Ber. (1961) 643, 128; CA99 (21): 175676W; CA 102(25): 216901S; CA 84(5): 29998b; CA83(26): 20942u]. None of these compounds, however, is dibenzylated. The compounds of the present invention are bis-biphenyl or phenylphthalamate substituted 3-mercapto-1,2,4-triazoles.

DETAILED DESCRIPTION OF THE INVENTION

The invention relates to bis-biphenyl substituted 3-thio-1,2,4-triazoles of the formula:

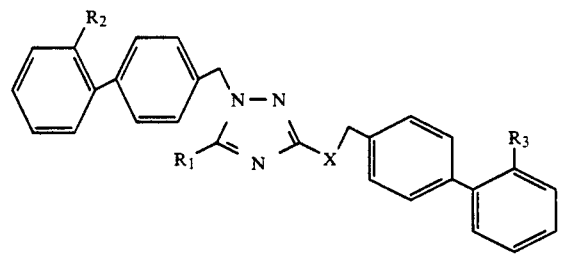

and

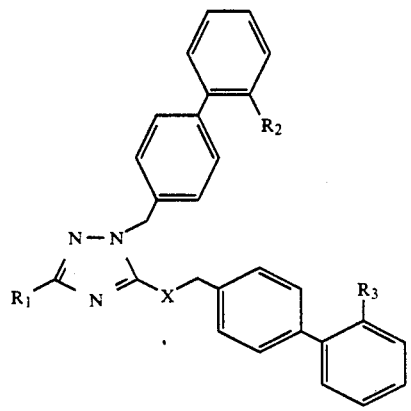

Wherein $R_1$ is selected from H, $C_{1-10}$ alkyl, $C_{2-10}$ alkenyl, benzyl, substituted benzyl wherein the substituent is selected from $C_{1-5}$ alkyl, $NO_2$ and halo such as chloro, bromo, fluoro or iodo; phenyl, phenylalkenyl such as 2-phenylethene or 2-phenylpropylene and substituted phenyl wherein the substituent is selected from $C_{1-5}$ alkyl, $NO_2$, $C_{1-6}$ alkoxy and halo such as chloro, bromo, fluoro or iodo;

$R_2$ and $R_3$ are the same or different and are selected from $CO_2H$, $CO_2C_{1-5}$ alkyl, CN, $CONH_2$, $CON(R_4)_2$ wherein $R_4$ is $C_{1-6}$ alkyl; 5-tetrazolo, CONHOH and $CONR_4OH$, wherein $R_4$ is $C_{1-6}$ alkyl, $CONHR_4$ wherein $R_4$ is 5-tetrazolo:

and X is selected from S, SO and $SO_2$.

The preferred compounds of the invention are those compounds wherein $R_1$ is $C_{1-10}$ is alkyl; $R_2$ is COOH or 5-tetrazolo and $R_3$ is $CO_2H$, CN or $CO_2C_{1-6}$ alkyl.

The preferred species of the invention are following compounds:

Disodium 5-butyl-1,3-bis[4-(2'-carboxyphenyl)benzyl]mercapto-1,2,4-triazole; 5-pentyl-1,3-bis[4-(2'-carboxyphenyl)benzyl]mercapto-1,2,4-triazole; 3-[4-(2'-carbomethoxyphenyl)benzyl]mercapto-5-pentyl-1-[4-(2'-tetrazolophenyl)benzyl]-1,2,4-triazole. 3-[4-(2'-cyanophenyl)benzyl]mercapto-5-pentyl-1-[4-(2'-tetrazolo-phenyl)benzyl]-1,2,4-triazole; and 1-[(2'-carboxyphenyl)benzyl]-3-[(2'-carboxyphenyl)benzylsulfonyl]-5-heptyl-1,2,4-triazole.

The invention also relates to a novel process for preparing the novel compounds as disclosed in Scheme 1.

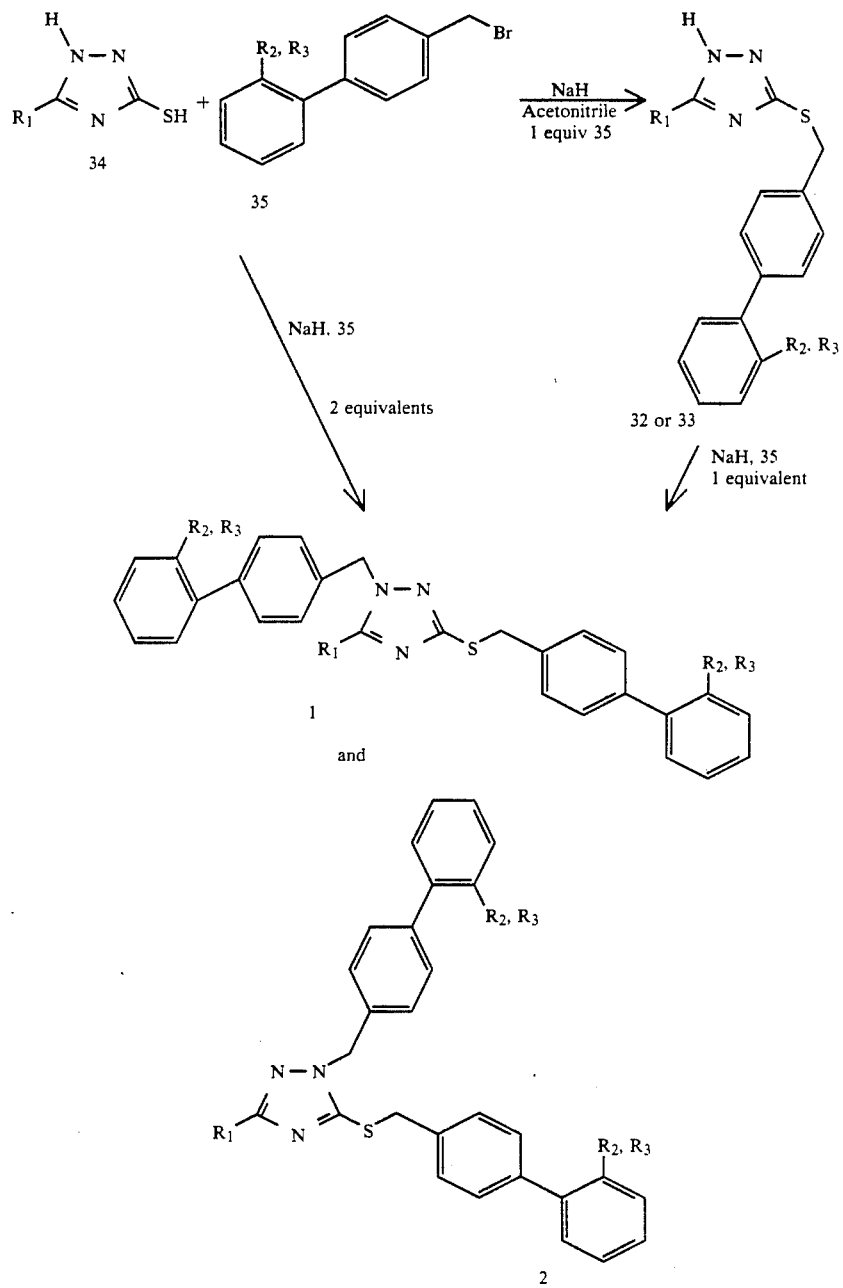

Scheme 1

As can be seen from Scheme 1 those compounds wherein X is S are prepared by first reacting a substituted mercaptotriazole with a substituted biphenylylhalide in a suitable solvent such as, for example, acetonitrile, dimethyformamide and alcohols such as methanol, in presence of a base such as, for example, sodium hydride, sodium hydroxide, potassium hydroxide, potassium hydride and potassium carbonate. The reaction mixture is stirred for from about 1-16 hours after which the solvent is removed in vacuo or by other means known to those skilled in the art. The residue is dissolved in an appropriate solvent such as, for example, ether, ethyl acetate or methylene chloride or tetrahydrofuran, and the solution is washed with dilute acid such as, for example, dilute hydrochloric acid, and then washed with water or brine. The solvent is dried and the product is collected by methods known to those skilled in the art; for example, the solution can be crystallized or chromotographed over ad adsorbent material such as, for example, silica gel and the product eluted with a suitable solvent. The product obtained is then reacted with a second equivalent of the base and the biphenylylhalide to obtain the substituted triazoles. If in the reaction scheme, two equivalents of the base and the biphenylylhalide are employed, the substituted triazoles are obtained directly and separated and purified by methods known to those skilled in the art.

The compounds wherein $R_2$ or $R_3$ is $CONH_2$, $CON(R_4)_2$, $CONHR_4$, $CONHOH$ or $CONR_4OH$ are prepared by: (1) converting structure 1 or 2 to an appropriate acid chloride as essentially described in W. Murray et al., in *Synthesis*, (1), 18 (1991) using oxalyl chloride or thionyl chloride in a solvent such as methylene chloride or THF. The acid chloride formed is then added to a solution of the amine such as $HN(C_{1-6}$ alkyl$)_2$, $NH_2(C_{1-6}$ alkyl), benzylamine, 5-aminotetrazole or amine hydrochloride such as $NH_2OH.HCl$, $NH(C_{1-6}$ alkyl)OH in an appropriate solvent such as methylene chloride or THF and a base such as triethylamine or pyridine. The amide will generally precipitate out of solution. Hydroxamides wherein $R_2$ or $R_3$ is CONHOH or $CONR_4OH$ are isolated by washing with water or dilute acid such as dilute hydrochloric acid, separation of layers, and concentration under reduced pressure.

The pharmaceutically acceptable salts of the invention include the sodium, potassium and pyridinium salts which are prepared by methods known to those skilled in the art.

The compounds of the invention where X is SO or $SO_2$ are prepared by dissolving a compound of structure 1 or 2 in an appropriate solvent such as methylene chloride of tetrachloroethylene. The solution is cooled to between 0° and 10° C. and a solvent such as methylene chloride or tetrachloroethylene is added dropwise. To generate the sulfoxide (S=SO) 1 equivalent of meta-chloroperbenzoic acid in an appropriate solvent (MCPBA) is used. To generate the sulfone ($SO_2$) two or more equivalents of MCPBA are used. Once the addition is complete the mixture is stirred for between 0 and 6 hours at between 0° and 25° C. Dilute base such as 10% NaOH or 5% KOH is added and the layers are separated. The organic layer is then washed with brine or water, dried over an appropriate drying agent, such as sodium sulfate or magnesium sulfate, filtered and concentrated in vacuo. The residue is then crystallized from an appropriate solvent such as ethyl acetate or ether or a solvent pair such as ethyl acetate/hexane or ether/hexane to afford the pure compound.

The biphenylylbromides 35 were prepared by the method of Duncia, et al. J. Org. Chem. 1991, 56, 2395-2400 or Aldrich et al U.S. Pat. Nos. 4,870,186 and 4,874,867. The substituted mercaptotriazoles 34 were prepared as described by Von Beyer et al., Leibigs Ann. 637, 135 (1960).

The compounds of this invention are angiotensin II receptor antagonists, and are useful in treating hypertension (lowering high blood pressure), congestive heart failure, elevated ocular pressure, cerebral stroke, angina, cardiac insufficiency, myocardial infarction and/or diabetic nephropathy.

Pharmaceutical compositions comprising a compound of the invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in oral dosage form, any of the usual pharmaceutical media may be employed. For example, in the case of oral liquid preparations (such as suspensions, elixirs and solution), water, glycols, oils, alcohol, flavoring agents, preservatives, coloring agents and the like may be used. In the case of oral solid preparations (such as, for example, powders, capsules and tablets), carriers such as starches, sugars, diluents, granulating agents, lubricants, binders, disintegrating agents and the like, may be used. Because of their ease in administration, tablets and capsules represent the most advantageous oral dosage unit form, in which case solid pharmaceutical carriers are preferably employed. If desired, tablets may be sugar-coated or enteric-coated by standard techniques. For parenterals, the carrier will usually comprise sterile water, through other ingredients, for example, to aid solubility or for preservative purposes, may be included. Injectable suspensions may also be prepared, in which case appropriate liquid carriers, suspending agents and the like may be employed. The pharmaceutical compositions will generally be in the form of a dosage unit, e.g., tablet, capsule, powder, injection, teaspoonful and the like, containing from 0.1 to about 1000 mg/kg, and preferably from about 1 to 200 mg/kg of the active ingredient.

The following experimental examples describe the invention in greater particularity and are intended to be a way of illustrating but not limiting the invention.

· In The Examples

Melting points were determined on a Thomas-Hoover apparatus and are uncorrected. The infrared spectra (R) were recorded on a Beckman Instruments IR-B spectrophotometer and are expressed in reciprocal centimeters ($cm^{-1}$). Nuclear magnetic resonance (NMR) spectra for hydrogen atoms were measured in the indicated solvent with tetramethylsilane (TMS) as the internal standard on a GE QE 300, a Bruker AC 300 or an IBM WP-100 spectrometer. The values are express in parts per million downfield from TMS. EI and CI mass spectra were obtained on a Finnigan MAT 8230 Double Focusing high resolution mass spectrometer.

EXAMPLE 1

5-Pentyl-3-[4-(2'-carbomethoxyphenyl)benzyl]mercapto-1,2,4-triazole 32

A mixture of 3-mercapto-5-pentyl-1,2,4-triazole (3.42 g. 0.02 mole), sodium hydride 80% in oil (1.0 g, 0.033 mole) and 4-(2'-carbomethoxyphenyl)benzylbromide (6.1 g, 0.02 mole) was stirred for 6 h in acetonitrile (300 mL). The resultant mixture was then filtered through celite, and rotovapped to a brown residue. The residue was chromatographed on silica gel using hexane/40% ethyl acetate as the mobile phase. Concentration of the eluates afforded 6.5 g (82%) of the title compound as a low melting, white, waxy solid. $^1$HNMR (CDCl$_3$) 7.82 (1H, d, J=7 Hz); 7.60–7.20 (7H, m); 4.38 (2H, s); 3.63 (3H, s); 2.78 (2H, t, J=7 Hz); 1.70 (2H, m); 1.4 (4H, m); 1.31 (3H, t, J=4 Hz). Mass Spec (DCI) m/z 396 (M+H). Analysis calc'd for $C_{22}H_{25}N_3O_2S$: C,66.82; H,6.32, N,10.00. found: C,66.67;H,6.34;N,10.00.

EXAMPLE 2

5-Pentyl-3-[4-(2'-cyanophenyl)benzyl]mercapto-1,2,4-triazole 33

The title compound was prepared following the procedure of Example 1 using 4-(2-cyanophenyl-benzylbromide as the biphenylylbromide, Yield 88%, mp 105°–106° C. Mass Spec (DCI) m/z 363 (M+H). Analysis calc'd for $C_{21}H_{22}N_4S$: C,69.56; H,6.12; N,15.46. found: C,69.59; H,5.91; N,15.34.

EXAMPLE 3

5-Pentyl-2,3-bis-[4-(2'-carbomethoxyphenyl)benzyl]mercapto-1,2,4-triazole 21 and 5-Pentyl-1,3-bis-[4-(2'-carbomethoxyphenyl)benzyl]mercapto-1,2,4-triazole 5.

A) A mixture of 5-pentyl-3-[4-(2'-carbomethoxyphenyl)benzyl]mercapto-1,2,4-triazole (3.95 g, 0.01 mole), sodium hydride 80% (0.5 g, 0.01 mole) and 4-(2-carbomethoxyphenyl)benzylbromide (3.04 g, 0.01 mole) were combined in 350 mL of acetonitrile and the mixture was refluxed for 5 h. The resulting mixture was filtered through celite and rotovapped to a brown residue. The residue was chromatographed on silica gel using hexane/30% ethyl acetate as the mobile phase. Concentration of the eluates afforded 5-pentyl-2,3-bis-[4-(2'-carbomethoxyphenyl)benzyl]mercapto-1,2,4-triazole 21 as a colorless oil (1.36 g, 22%) and 5-pentyl-1,3-bis-[4-(2'-carbomethoxyphenyl)benzyl]mercapto-1,2,4-triazole 5 as a colorless oil (2.52 g, 41%).

B) A mixture of 3-mercapto-5-pentyl-1,2,4-triazole (1.71 g, 0.01 mole), sodium hydride, 80% in oil (1.0 g, 0.033 mole) and 4-(2'-carbomethoxyphenyl)benzylbromide (6.1 g, 0.02 mole) was refluxed for 8 h in acetonitrile (300 mL). The resultant mixture was then filtered through celite, and rotovapped to a brown residue. The residue was chromatographed on silica gel using hexane/30% ethyl acetate as the mobile phase. Concentration of the eluates afforded 5-pentyl-2,3-bis-[4-(2'-carbomethoxyphenyl)benzyl]mercapto-1,2,4-triazole 21 (0.9 g, 15%) and 5-pentyl-1,3-bis-[4-(2'-carbomethoxyphenyl)benzyl]mercapto-1,2,4-triazole 5 (1.02 g, 16%) as colorless oils.

Compound 21: $^1$NMR (CDCl$_3$) 7.82 (2H, m); 7.6–7.2 (14H, m); 5.16 (2H, s); 4.51 (2H, s); 3.63 (3H, s); 3.60 (3H,s); 2.76 (2H, t, J=7 Hz); 1.78 (2H, m); 1.40 (4H, m); 1.31 (3H, m). Mass Spec (DCI) m/z 620 (M+H). Analysis calc'd for $C_{37}H_{37}N_3O_4S.\frac{1}{2}$ H$_2$O: C,70.68; H,6.09; N,6.68. found: C,70.47; H,5.59; N,6.90.

Compound 5: $^1$HNMR (CDCl$_3$) 7.82 (2H, m); 7.6–7.15 (14H, m); 5.24 (2H, s); 4.41 (2H, s); 3.62 (3H, s); 3.60 (3H, s); 2.67 (2H, t, J=7 Hz); 1.65 (2H, m); 1.35 (4H, m); 0.85 (3H, t, J=4 Hz). NOE enhancement of 2.67 t when 5.24 s irradiated. Mass Spec (DCI) m/z 620 (M+H). Analysis calc'd for $C_{37}H_{37}N_3O_4S$. H$_2$O: C,69.69; H,6.16; N,6.59. found: C,69.32; H,6.00; N,6.86.

EXAMPLE 4

5-Butyl-2,3-bis-[4-(2'-carbomethoxyphenyl)benzyl]mercapto-1,2,4-triazole 17

5-Butyl-1,3-bis-[4-(2'-carbomethoxyphenyl)benzyl]mercapto-1,2,4-triazole 1

The title compounds were prepared by following the procedure of Example 3.

Compound 17: Mass Spec (DCI) m/z 606 (M+H). Analysis calc'd for $C_{36}H_{35}N_3O_4S.\frac{1}{2}$ H$_2$O: C,70.34; H,5.90; N,6.83. found: C,70.60; H,6.06; N,7.12.

Compound 1: Mass Spec (DCI) m/z 606 (M+H). Analysis calc'd for $C_{36}H_{35}N_3O_4S$: C,71.39; H,5.82; N,6.94. found: C,70.90; H,5.22; n,7.16.

EXAMPLE 5

5-Isobutyl-2,3-bis-[4-(2'-carbomethoxyphenyl)benzyl]-mercapto-1,2,4-triazole 19

5-Isobutyl-1,3-bis-[4-(2'-carbomethoxyphenyl)benzyl]-mercapto-1,2,4-triazole 3

The title compounds were prepared by following the procedure (B) of Example 3.

Compound 19: Mass Spec (DCI) m/z 606 (M+H).

Compound 3; Mass Spec (DCI) m/z 606 (M+H). Analysis calc'd for $C_{36}H_{35}N_3O_4S.\frac{1}{2}$ H$_2$O: C,70.34; H,5.90; N,6.83. found: C,70.30, H,5.66; N,7.12.

EXAMPLE 6

5-Hexyl-2,3-bis-[4-(2'-carbomethoxyphenyl)benzyl]-mercapto-1,2,4-triazole 24

5-Hexyl-1,3-bis-[4-(2'-carbomethoxyphenyl)benzyl]-mercapto-1,2,4-triazole 8

The title compounds were prepared by following the procedure (B) of Example 3.

Compound 24: Mass Spec (DCI) m/z 634 (M+H)

Compound 8: Mass Spec (DCI) m/z 634 (M+H). Analysis calc'd for $C_{38}H_{39}N_3O_4S.\frac{1}{2}$ H$_2$O: C,71.00; H,6.27; N,6.53. found: C,70.96; H,6.47; Nm6.81.

EXAMPLE 7

5-Heptyl-2,3-bis-[4-(2'-carbomethoxyphenyl)benzyl]-mercapto-1,2,4-triazole 25

5-Heptyl-1,3-bis-[4-(2'-carbomethoxyphenyl)benzyl]-mercapto-1,2,4-triazole 9

The title compounds were prepared by following the procedure (B) of Example 3.

Compound 9: Mass Spec (DCI) m/z 684 (M+H). Analysis calc'd for $C_{39}H_{41}N_3O_4S.\frac{1}{2}$ H$_2$O: C,71.32; H,6.44; N,6.40. found: C,71.31; H,6.38; 6.96.

Compound 25: Mass Spec (DCI) m/z 648 (M+H). Analysis Calc'd for $C_{39}H_{41}N_3O_4S.\frac{1}{2}$ H$_2$O: C,71.32; H,6.44; N,6.40. found: C,71.25; H,6.73; N,6.63.

EXAMPLE 8

3-[(2'-Cyanophenyl)benzyl]mercapto]-2-(2'-carbomethoxyphenyl)benzyl-5-butyl-1,2,4-triazole 28

3-[(2'-Cyanophenyl)benzyl]mercapto]-1-(2'-carbomethoxyphenyl)benzyl-5-butyl-1,2,4-triazole 13

The title compounds were prepared by following procedure (A) of Example 3 using compound 33 in place of compound 32.

Compound 28; Mass Spec (DCl) m/z 573 (M+H). Analysis calc'd for $C_{35}H_{32}N_4O_2S.0.25\ H_2O$: C,72.81; H,5.68; N,9.70. found: C,72.66; H,5.79; N,9.92.

Compound 13: Mass Spec (DCl) m/z 573 (M+H). Analysis calc'd for $C_{35}H_{32}N_4O_2S.0.25\ H_2O$: C,72.81; H,5.68; N,9.70. found: C,72.81; H,5.78; N,10.15.

EXAMPLE 9

5-Benzyl-2,3-bis-[4-(2'-carbomethoxyphenyl)benzyl]-mercapto-1,2,4-triazole 27

The title compound was prepared by following the procedure (B) of Example 3.

Compound 27: Mass Spec (DCl) m/z 640 (M+H). Analysis calc'd for: C,73.22; H,5.20; N,6.57. found: C,73.16; H,5.25; N,6.10.

EXAMPLE 10

3-[(2'-Cyanophenyl)benzyl]mercapto]-1-(2'-carbomethoxyphenyl)benzyl-5-pentyl-1,2,4-triazole 14

The title compound was prepared by following the procedure of Example 8.

Compound 14: Mass Spec (DCl) m/z 587 (M+H). Analysis calc'd for $C_{36}H_{34}N_4O_2S$: C,73.69; H,5.84; N,9.55. found: C,73.54; H,5.94; N,9.46.

EXAMPLE 11

5-Pentyl-1,3-bis-[4-(2'-carboxyphenyl)benzyl]mercapto-1,2,4-triazole 6

5-Pentyl-1,3-bis[4-(2'-carbomethoxyphenyl)benzyl]-mercapto-1,2,4-triazole (1.24 g, 0.002 mole) was dissolved in methanol (35 mL), 30% KOH (10 mL) was added to this solution and the reaction was refluxed for 8 h. The resultant mixture was concentrated in vacuo and partitioned between methylene chloride and water (50 mL each). The methylene chloride layer was removed and the aqueous layer was acidified to pH 1 with dilute HCl. The aqueous layer was extracted with 3 portions of methylene chloride (50 mL each), dried over sodium sulfate, filtering and concentrated to a yellow foam (1.0 g, (83%). Mass Spec (DCl) m/z 592 (M+H). Analysis calc'd for $C_{35}H_{32}N_3O_4S.2H_2O$; C,66.97; H,5.63; N,6.69. found: C,67.06; H,5.76; N,6.39.

EXAMPLE 12

5-Pentyl-2,3-bis-[4-(2'-carboxyphenyl)benzyl]mercapto-1,2,4-triazole 23

The title compound was prepared according to the procedure of Example 11. Yield 72%, mp 116°–120° C. Mass Spec (DCl) m/z 592 (M+H). Analysis calc'd for $C_{35}H_{32}N_3O_4S.H_2O$: C,68.85; H,5.79; N,6.89. found: C,68.80; H,5.41; N,7.12.

EXAMPLE 13

5-Butyl-1,3-bis-[4-(2'-carboxyphenyl)benzyl]mercapto-1,2,4-triazole 18

The title compound was prepared according to the procedure of Example 11. mp 118°–122° C. Mass Spec (DCl) m/z 578 (M+H). Analysis calc'd for $C_{34}H_{31}N_3O_4S$: C,70.70; H,5.41; N,7.27. found: C,70.17; H,5.00; N,7.29.

EXAMPLE 14

Disodium 5-Butyl-1,3-bis-[4-(2'-carboxyphenyl)benzyl]mercapto-1,2,4-triazole 2

The title compound was prepared according to the procedure of Example 11. The sodium salt was formed by dissolving the triazole in methanol containing 2 equivalents of sodium methoxide and subsequent concentration in vacuo. mp 235° C. Mass Spec (DCl) m/z 578 (M+H). Analysis calc'd for $C_{34}H_{29}N_3O_4SNa_2.1.25\ H_2O$: C,63.39; H,4.93; N6.50; found: C,63.11; H,4.90; N,6.89.

EXAMPLE 15

Sodium 5-isobutyl-1,3-bis-[4-(2'-carboxyphenyl)benzyl]mercapto-1,2,4-triazole 4

The title compound was prepared according to the procedure of Example 11. The sodium salt was formed by dissolving the triazole in methanol containing 1 equivalent of sodium methoxide and subsequent concentration in vacuo. mp 143° C. (dec.). Mass Spec (DCl) m/z 578 (M+H). Analysis calc'd for $C_{34}H_{30}N_3O_4SNa.2\ H_2O$: C,64.23; H,5.23: N,6.60; found: C,64.66; H,4.99; N,6.69.

EXAMPLE 16

Sodium 5-isobutyl-2,3-bis-[4-(2'-carboxyphenyl)benzyl]mercapto-1,2,4-triazole 20

The title compound was prepared according to the procedure of Example 11. The sodium salt was formed by dissolving the triazole in methanol containing 1 equivalent of sodium methoxide and subsequent concentration in vacuo. mp 140° C. (dec.). Mass Spec (DCl) m/z 578 (M+H). Analysis calc'd for $C_{34}H_{30}N_3O_4SNa.H_2O$: C,66.10; H,5.38; N,6.80. found: c,65.81; H,5.10; N,6.84;

EXAMPLE 17

5-Heptyl-1,3-bis-[4-(2'-carboxyphenyl)benzyl]mercapto-1,2,4-triazole 10

The title compound was prepared according to the procedure of Example 11. mp 78°–80° C. Mass Spec (DCl) m/z 620 (M+H). Analysis calc'd for $C_{37}H_{37}N_3O_4S.2\ H_2O$: C,67.77; H,6.30; N,6.41. found: c,68.09; H,6.17; N,5.98.

EXAMPLE 18

Sodium 5-isobutyl-2,3-bis-[4-(2'-carboxyphenyl)benzyl]mercapto-1,2,4-triazole 26

The title compound was prepared following the procedure of Example 11. The sodium salt was formed by dissolution in methanol containing 1 equivalent of sodium methoxide and subsequent concentration in vacuo. mp 110° C. (dec.). Mass Spec (DCl) m/z 620 (M+H). Analysis calc'd for $C_{37}H_{36}N_3O_4SNa.1.5H_2O$: C,66.45; h,6.02; N,6.28. found: C,66.27; H,5.59; N,6.12.

EXAMPLE 19

5-Benzyl-2,3-bis-[4-(2'-carboxyphenyl)benzyl]mercapto-1,2,4-triazole 11

The title compound was prepared according to the procedure of Example 11. Mass Spec (DCl) m/z 612 (M+H). Analysis calc'd for $C_{37}H_{29}N_3O_4S.0.4\ H_2O$: C,71.80; H,4.85; N,6.79. found: C,72.02; H,5.14; N,6.39.

EXAMPLE 20

3-[4-(2'-Cyanophenyl)benzyl]mercapto]-1-[4-(2'-carboxyphenyl)benzyl]-5-pentyl-1,2,4-triazole 12

5-Pentyl-1,3-bis-[4-(2'-carboxyphenyl)benzyl]mercapto-1,2,4-triazole (1.18 g, 0.002 mole) was dissolved in methanol (35 mL). 30% KOH (10 mL) was added to this solution and the reaction mixture was refluxed for 2 h. The resultant mixture was concentrated in vacuo and partitioned between methylene chloride and water (50 mL each). The methylene chloride layer was removed and the aqueous layer was acidified to pH 1 with dilute HCl. The aqueous layer was extracted with 3 portions of methylene chloride (50 mL each), dried over sodium sulfate, filtered and concentrated to a white foam (1.0 g, 88% yield). Mass Spec (DCl) m/z 573 (M+H). Analysis calc'd for $C_{35}H_{32}N_4O_2S.0.25\ H_2O$: C,72.83; H,5.68; N,9.71. found: C,72.58; H,5.66; N,9.68.

EXAMPLE 21

1-[(2'-Cyanophenyl)benzyl]-3-[4-(2'-carboxyphenyl)benzyl]mercapto-5-pentyl-1,2,4-triazole 15

The title compound was prepared according to the procedure of Example 20, Yield 80%. Mass Spec (DCl) m/z 573 (M+H). Analysis calc'd for $C_{35}H_{32}N_4O_2S.0.5\ H_2O$: C,72.26; H,5.72; N,9.63. found: C,72.25; H,5.69; N,9.56.

EXAMPLE 22

3-[(2'-Cyanophenyl)benzyl]mercapto]-2-[4-(2'-carboxyphenyl)benzyl]-5-butyl-1,2,4-triazole 29

The title compound was prepared according to the procedure of Example 20, Yield 89%. Mass Spec (DCl) m/z 559 (M+H). Analysis calc'd for $C_{34}H_{30}N_4O_2S.0.5\ H_2O$: C,71.37; H,5.55; N,9.79. found: C,71.28; H,5.64; N,9.61.

EXAMPLE 23

3-[4-(2'-Cyanophenyl)benzyl]mercapto-5-pentyl-1-{4-[2'-(1-triphenylmethyltetrazolophenyl)benzyl]-1,2,4-triazole 43

3-[4-(2'-Cyanophenyl)benzyl]mercapto-5-pentyl-2-{4-[2'-(1-triphenylmethyltetrazolophenyl)benzyl]-1,2,4-triazole 44

The title compounds were prepared according to the procedure of Example 8 using 5-pentyl-3-[4-(2'-cyanophenyl)benzyl]mercapto-1,2,4-triazole and 4-[2'-(1-triphenylmethyltetrazolophenyl)benzyl]bromide (Aldrich et al. U.S. Pat Nos. 4,870,186 and No. 4,874,867).

Compound 43: NMR (CDCl3) shows characteristic benzylic peaks at 5.12 (2H, s) and 4.35 (2H, s). Compound 44: NMR (CDCl3) shows characteristic benzyl peaks at 5.00 (2 H, s) and 4.38 (2H, s).

EXAMPLE 24

3-[4-(2'-Cyanophenyl)benzyl]mercapto-5-pentyl-1-[4-(2'-tetrazolophenyl)benzyl]-1,2,4-triazole hemihydrate 36

3-[4-(2'-Cyanophenyl)benzyl]mercapto-5-pentyl-1-[4-(2'-triphenylmethyltetrazolophenyl)benzyl]-1,2,4-triazole (0.6 g) was dissolved in THF (15 mL). 3N HCl (5 mL) was added to this solution and the resultant solution was stirred for 16 h at room temperature. The solution was then poured into 50 mL of ether. The ether layer was washed twice with 10% HCl, dried over sodium sulfate, filtered and concentrated to an oil which was chromatographed on silica gel using hexane/40% ethyl acetate as the mobile phase. Concentration in vacuo afforded 320 mg (75%) of a white foam found to be the title compound. Mass Spec (DCl) m/z 597 (M+H). Analysis calc'd for: $C_{35}H_{32}N_8S.0.5\ H_2O$: C, 69.40; H,5.49; N, 18.50. found: C, 69.43; H, 5.27; N, 18.84.

EXAMPLE 25

3-[4-(2'-Carbomethoxyphenyl)benzyl]mercapto-5-pentyl-1-{4-[2'-(1-triphenylmethyltetrazolo)phenyl]benzyl}-1,2,4-triazole 45

3-[4-(2'-Carbomethoxyphenyl)benzyl]mercapto-5-pentyl-2-{4-[2'-(1-triphenylmethyltetrazolo)phenyl]benzyl}-1,2,4-triazole 46

The title compounds were prepared according to the procedure of Example 8 using 5-pentyl-3-[4-(2'-carbomethoxyphenyl)benzyl]mercapto-5-pentyl-1,2,4-triazole and 4-[2'-(1-triphenylmethyltetrazolo)phenyl]benzyl}bromide (Aldrich et al. U.S. Pat. Nos. 4,870,186 and No. 4,874,867). Compound 45: NMR (CDCl3) shows characteristic benzylic peaks at 5.14 (2H, s) and 4.34 (2H, s). Compound 46: NMR (CDCl3) shows characteristic benzylic peaks at 5.00 (2H, s) and 4.40 (2H, s).

EXAMPLE 26

3-[4-(2'-Carbomethoxyphenyl)benzyl]mercapto-5-pentyl-1-[4-(2'-tetrazolophenyl)benzyl]-1,2,4-triazole hemihydrate 16.

The title compound was prepared according to the procedure of Example 24 using compound 45 in place of compound 43 and was obtained as a white foam, Yield 72%. Mass Spec. (DCl) m/z 630 (M+H). Analysis calc'd for: $C_{35}H_{32}N_8S.0.5\ H_2O$ C, 67.69; H,5.68; N, 15.35. found: C, 67.72; H,5.69; N, 15.11

EXAMPLE 27

1-[(2'-Carbomethoxyphenyl)benzyl]-3-[(2'-carbomethoxyphenyl)benzyl]mercapto-5-hexyl-1,2,4-triazole hemihydrate 7

2-[(2'-Carbomethoxyphenyl)benzyl]-3-[(2'-carbomethoxyphenyl)benzyl]mercapto-5-hexyl-1,2,4-triazole hydrate 24

The title compounds were prepared according to the procedure of Example 3. Compound 7: Mass Spec (DCl) m/z 634 (M+H). Analysis calc'd for: $C_{38}H_{39}N_3O_4.H_2O$: C, 71.00; H, 6.27; N,6.53. found: C, 70.96; H,6.47, N,6.81. Compound 24: Mass Spec (DCl) m/z 634 (M+H).

EXAMPLE 28

1-[(2'-Carbomethoxyphenyl)benzyl]-3-[(2'-carbomethoxyphenyl)benzylsulfonyl]-5-hexyl-1,2,4-triazole hydrate 37

1-[(2'-Carbomethoxyphenyl)benzyl]-3-[(2'-carbomethoxyphenyl)benzylmercapto]-5-hexyl-1,2,4-triazole hemihydrate (0.2 g, 0.3 mM) was dissolved in methylene chloride and cooled to 0° C. To this solution was added dropwise, a solution of meta-chloroperbenzoic acid (138 mg, 0.8 mM) in 20 mL of methylene chloride. The solution was stirred at 10° C. for 2 h. 10 mL of 1N NaOH was added and the layers were separated. The organic layer was washed with brine, dried over sodium sulfate, filtered and concentrated to a solid which was recrystallized from ethyl acetate/hexane to afford a white solid, mp 103°–105° C.

(0.16 g, 76%). Mass Spec. (DCI) m/z 666 (M+H). Analysis: calc'd for $C_{38}H_{39}N_3O_6S.H_2O$: C, 68.56; H, 5.90; N, 6.31. found: C, 68.37; H, 5.87; N, 6.50.

EXAMPLE 29

1-[(2'-Carbomethoxyphenyl)benzyl]-3-[2'-carbomethoxyphenyl)benzylmercapto]-5-octyl-1,2,4-triazole hydrate 47

2-[(2'-Carbomethoxyphenyl)benzyl]-3-[(2'-carbomethoxyphenyl)benzylmercapto]-5-octyl-1,2,4-triazole hydrate 48

The title compounds were prepared according to the procedure of Example 3. Compound 47: Mass Spec: (DCI) m/z 662 (M+H). Compound 48: Mass Spec: (DCI) m/z 662 (M+H).

EXAMPLE 30

1-[(2'-Carbomethoxyphenyl)benzyl]-3-[(2'-carbomethoxyphenyl)benzylsulfonyl]-5-octyl-1,2,4-triazole hydrate 49

The title compound was prepared according to the procedure of Example 28 Mass Spec. (DCI) m/z 694 (M+H). Analysis calc'd for: $C_{40}H_{43}N_3O_6.H_2O$: C,67.50; H,6.37; N,5.90. found: C,67.72; H,6.05; N, 6.24.

EXAMPLE 31

1-[(2'-Carboxyphenyl)benzyl]-3-[(2'-carboxyphenyl)benzylsulfonyl]-5-octyl-1,2,4-triazole hydrate 38

The title compound was prepared according to the procedure of Example 11 and was isolated as a white solid, mp 125°–128° C. Mass Spec. (DCl) m/z 666 (M+H).

EXAMPLE 32

1-[(2'-Carbomethoxyphenyl)benzyl]-3-[(2'-carbomethoxyphenyl)benzylsulfonyl]-5-heptyl-1,2,4-triazole 50.

The title compound was prepared according to the procedure of Example 28 and was isolated as a white solid, mp 93°–95° C. Mass Spec (DCI) m/z 680 (M+H). Analysis calc'd for $C_{39}H_{41}N_3O_6S$: C,68.19; H, 5.72; N,6.45. found C, 68.55; H, 6.27; N, 6.13.

EXAMPLE 33

1-[(2-Carboxyphenyl)benzyl]-3-[(2'-carboxyphenyl)benzylsulfonyl]-5-heptyl-1,2,4-triazole hydrate 39

The title compound was prepared according to the procedure of Example 11 and was isolated as a white solid, mp 158°–160° C. Mass Spec. (DCl) m/z 652

EXAMPLE 34

1-[(2'-Carboxyphenyl)benzyl]-3-[(2'-carboxyphenyl)benzylsulfonyl]-5-hexyl-1,2,4-triazole 0.5 hydrate 40

The title compound was prepared according to the procedure of Example 11 and was isolated as a white solid, mp 118°–120° C. Mass Spec. (DCl) m/z 638 (N+H). Analysis calc'd for: $C_{36}H_{35}N_3O_6S.0.5 H_2O$: C, 66.86; H,5.58; N, 6.49; found: C, 66.62; H,5.72; N,6.25.

EXAMPLE 35

1-[(2'-Carbomethoxyphenyl)benzyl]-3-[(2'-carbomethoxyphenyl)benzylmercapto]-5-(2-phenyl-1,2,4-triazole 41

2-[(2'-Carbomethoxyphenyl)benzyl]-3-[(2'-carbomethoxyphenyl)benzylmercapto]-5-(2-phenyl)-1,2,4-triazole 42

The title compounds were prepared according to the procedure of Example 3. Compound 41: Mass Spec (DCI) m/z 652 (M+H). Analysis calc'd for $C_{40}H_{33}N_3O_4S$: C, 73.71; H,5.10; N, 6.45 found: C,73.35; H,5.10; N,6.43. Compound 42: Mass Spec (DCI) m/z 652 (M+H). Analysis calc'd for: $C_{40}H_{33}N_3O_4S$: C, 73.71; H,5.10; N, 6.45. found: 73.46; H,5.45; N,6.21.

EXAMPLE 36

2-[(2'-Carbomethoxyphenyl)benzyl]-3-[(2'-carbomethoxyphenyl)benzylmercapto]-5-(2-phenyl)-1,2,4-triazole hydrate 30

The title compound was prepared according to the procedure of Example 3. Mass Spec (DCI) 626 (M+H). Analysis calc'd for: $C_{38}H_{31}N_3O_4S.H_2O$: C, 70.90; H,5.17; N,6.53. found: C,71.37; H,5.06; N,6.59.

EXAMPLE 37

2-[(2'-Carboxyphenyl)benzyl]-3-[(2'-carboxyphenyl)benzylmercapto]-5-phenyl-1,2,4-triazole hydrate 31

The title compound was prepared according to the procedure of Example 11. Mass Spec (DCl) m/z 598 (M+H). Analysis calc'd for: $C_{36}H_{27}N_3O_4S.H_2O$: C, 70.23; H, 4.75; N, 6.82. found: C,70.39; H, 4.99; N, 6.50.

TABLE 1

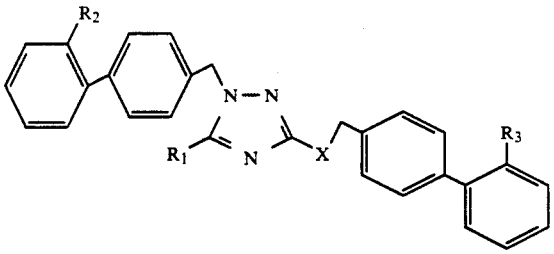

Structure 1

| Compound | $R_1$ | $R_2$ | $R_3$ | X |
|---|---|---|---|---|
| 1 | n-Bu | $CO_2Me$ | $CO_2Me$ | S |
| 2 | n-Bu | $CO_2Na$ | $CO_2Na$ | S |
| 3 | i-Bu | $CO_2Me$ | $CO_2Me$ | S |
| 4* | i-Bu | $CO_2Na$ | $CO_2H$ | S |
| 5 | n-pentyl | $CO_2Me$ | $CO_2Me$ | S |
| 6 | n-pentyl | $CO_2H$ | $CO_2H$ | S |
| 7 | n-hexyl | $CO_2Me$ | $CO_2Me$ | S |
| 8 | n-hexyl | $CO_2Me$ | $CO_2Me$ | S |
| 9 | n-heptyl | $CO_2Me$ | $CO_2Me$ | S |
| 10 | n-heptyl | $CO_2H$ | $CO_2H$ | S |
| 11 | benzyl | $CO_2H$ | $CO_2H$ | S |
| 12 | n-pentyl | $CO_2H$ | CN | S |

TABLE 1-continued

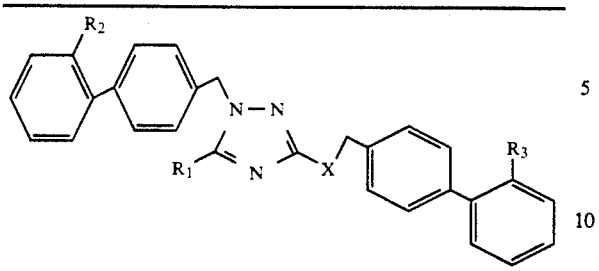

Structure 1

| Compound | R₁ | R₂ | R₃ | X |
|---|---|---|---|---|
| 13 | n-pentyl | CO₂Me | CN | S |
| 14 | n-pentyl | CN | CO₂Me | S |
| 15 | n-pentyl | CN | CO₂H | S |
| 16 | n-pentyl | tetrazolo | CO₂Me | S |
| 36 | n-pentyl | tetrazolo | CN | S |
| 37 | n-hexyl | CO₂Me | CO₂Me | SO₂ |
| 38 | n-octyl | CO₂H | CO₂H | SO₂ |
| 39 | n-heptyl | CO₂H | CO₂H | SO₂ |
| 40 | n-hexyl | CO₂H | CO₂H | SO₂ |
| 41 | 2-phenyl ethylene | CO₂Me | CO₂Me | S |
| 43 | n-pentyl | 1-trityl-tetrazolo | CN | S |
| 45 | n-pentyl | 1-trityl-tetrazolo | CO₂Me | S |
| 47 | n-octyl | CO₂Me | CO₂Me | S |
| 49 | n-octyl | CO₂Me | CO₂Me | SO₂ |

*Monosodium salt position not defined

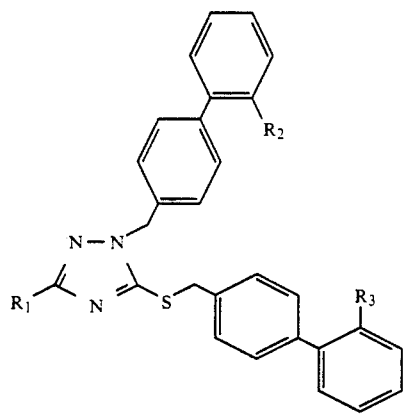

Structure 2

| Compound | R₁ | R₂ | R₃ |
|---|---|---|---|
| 17 | n-butyl | CO₂Me | CO₂Me |
| 18 | n-butyl | CO₂H | CO₂H |
| 19 | i-butyl | CO₂Me | CO₂Me |
| 20* | i-butyl | CO₂Na | CO₂H |
| 21 | n-pentyl | CO₂Me | CO₂Me |
| 23 | n-pentyl | CO₂H | CO₂H |
| 24 | n-hexyl | CO₂Me | CO₂Me |
| 25 | n-hexyl | CO₂Me | CO₂Me |
| 26* | isobutyl | CO₂Na | CO₂H |
| 27 | benzyl | CO₂Me | CO₂Me |
| 28 | n-pentyl | CO₂Me | CN |
| 29 | n-butyl | CO₂H | CN |
| 30 | phenyl | CO₂Me | CO₂Me |
| 31 | phenyl | CO₂H | CO₂H |
| 42 | 2-phenyl ethylene | CO₂Me | CO₂Me |
| 44 | n-pentyl | 1-trityl-tetrazolo | CN |
| 46 | n-pentyl | 1-trityl-tetrazolo | CO₂Me |

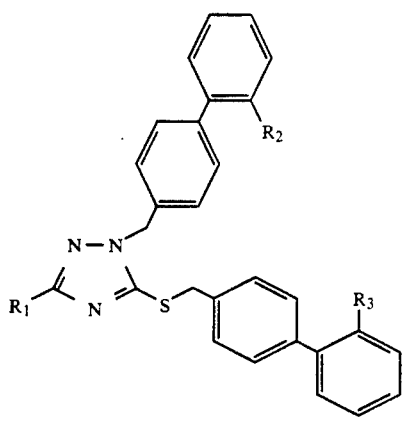

Structure 2

| Compound | R₁ | R₂ | R₃ |
|---|---|---|---|
| 48 | n-octyl | CO₂Me | CO₂Me |

*Monosodium salt position not defined

Biological Test Procedures

Inhibition of Angiotensin II Dose-Response in Rabbit Thoracic Aorta

Purpose: To identify competitive receptor antagonists of an angiotensin II-1 activity, i.e., angiotensin II-induced vasoconstriction in in vitro aortic rings.

Procedure: 1.8 to 2.3 kg New Zealand white rabbits are sacrificed with an intravenous sodium pentobarbital overdose and the thoracic aorta gently dissected free from the aortic root to the level of the diaphragm, into ice cold Krebs bicarbonate buffer. The aorta is gently freed of clots and adventitia and cleanly cut with a scalpel into 5 mm segments. Each ring is suspended from a Gould isotonic force transducer in a tissue bath containing 15 mL oxygenated Krebs bicarbonate buffer regulated at 37° C. Initial tension is adjusted to 4.0 g and equilibrated over three 20-min wash periods to achieve a baseline tension of 3.0 g. Graded angiotensin II doses are given cumulatively to achieve a maximal contraction. Three 20-min washes are performed to remove the initial angiotensin II effect. The test compound is then given at a screening concentration of $1.0 \times 10^{-5}$ M. After observing any effects of the test compound alone, the angiotensin II cumulative dose-response is then repeated in the presence of the test compound.

Analysis: Angiotensin II vasoconstrictor tension in grams is expressed as a percent of maximal contraction for the before and after test compound angiotensin II dose-responses. Angiotensin II ED50 and ED90 is determined from the angiotensin II dose-response curves generated before and after test compound. A percent inhibition of the angiotensin II dose-response is calculated by determining the percent of maximal contraction occurring after the test compound at the concentration that achieved a 90% contraction before antagonist: 90-percent contraction occurring after test compound at the ED90 before test compound/$90 \times 100 = \%$ Inhibition.

Controls: Test compounds are dissolved in DMSO vehicle and DMSO vehicle alone is tested in two rings as a vehicle control in each screening experiment. In this assay, vehicle alone shows a percent inhibition of $5.2 \pm 0.7 = \%$ (N=23 tests).

| Reference Compounds: | Compound | pA2 (95% C.L.) |
|---|---|---|
| | DuP-753 | 8.95 (8.57–9.33) |
| | Saralasin | 9.86 (9.21–10.51) |

Test Procedure for Screening Potential Angiotensin II Receptor

Antagonists in Salt-Depleted Normotensive Rats

Purpose: This test is designed to detect hypotensive effects of a compound after oral dosing in normotensive animals made renin-dependent by salt depletion.

Method: Male 350–450 g Sprague-Dawley rats are implanted with teflon microcannulae via the middle caudal artery under 20 mg/kg intravenous brevital anesthesia and permitted a 4–7 day surgical recovery period. Throughout recovery and testing animals are individually housed unrestrained in standard rat metabolism cages and receive continuous 0.5 ml/h intra-arterial 0.25N saline infusion through a spring-shielded swivelling tether connected to an infusion/blood pressure recording system to maintain arterial cannula patency. Animals are maintained on Low Sodium (0.03%) Purina Rat Chow #5881 throughout the study. After the recovery period animals are given oral 50 mg/kg furosemide (Lasix, Hoechst-Roussel Pharmaceutical) doses on two consecutive days to produce marked diuresis and plasma volume depletion that makes maintenance of normal blood pressure highly dependent on function of the renin-angiotensin-aldosterone system. Three hours after the second furosemide dose, rats are given test compound uniformly suspended in 1% methylcellulose (n=3/dose level) or 1 mL 1% methylcellulose vehicle (n=3) orally by gavage and blood pressure is continuously recorded for 24 h using a Buxco computerized data recording system. Compound-induced changes in blood pressure are compared to concurrent vehicle control blood pressures in order to detect drug effect.

Interpretation: Prior to salt depletion, normotensive rats typically show a plasma renin activity (PRA, ng angiotensin I/mL, plasma/h, RIA) of 0.7. After the salt-depletion protocol PRA values taken 3 h after the furosemide dose have risen to about 7.4. Whereas blood pressure of normotensive rats that have not been salt-depleted does not change in response to treatment with the nonpeptide angiotensin receptor antagonist, DuP-753, salt-depleted animals typically respond with a blood pressure decrease of about 35 mmHg (mean arterial pressure, MAP). PRA is increased by this DuP-753 treatment to about 41.4

Compounds that decrease blood pressure 10 or more mmHg (MAP) compared to concurrent control after oral dosing are considered active in this test. Maximum possible response is about −35 mmHg. Compounds that are not orally active ar retested by giving a solution dose intra-arterially through the blood pressure cannula three hours after a furosemide dose.

| | Biological Activity: | |
|---|---|---|
| Compound | % Inhib. @ 10 μM | pA2 |
| 2 | 100 | 8.49 |
| 4 | 100 | 7.49 |
| 6 | 100 | 8.39 |
| 8 | 100 | 7.96 |
| 9 | 2 | — |
| 10 | 97 | 6.73 |
| 12 | 79 | |
| 21 | 4 | |
| 23 | 100 | 7.19 |
| 25 | 1 | — |
| 26 | 48 | 5.88 |
| 16 | | 5.00 |
| 40 | 100 | 8.05 |
| 38 | 87 | 6.09 |
| 39 | 89 | 6.49 | pA2 is the negative logarithm of the antagonist concentration that causes a 2-fold shift to the right (i.e. decrease) in the potency of the agonist or the negative logarithm of the antagonist concentration that cuts the potency of the agonist in half.

What is claimed is:

1. A compound of the formula

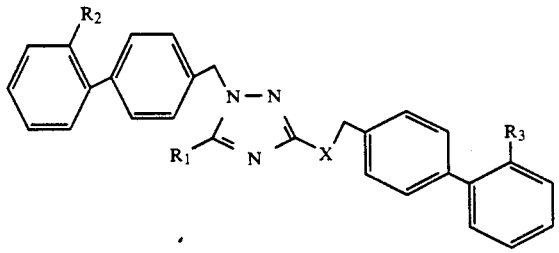

and

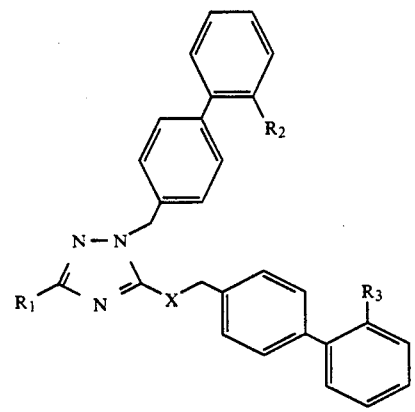

or pharmaceutically acceptable sodium, potassium or pyridinium salts thereof wherein $R_1$ is selected from H, $C_{1-10}$ alkyl, $C_{2-10}$ alkenyl, benzyl, 2-phenylethenyl, substituted benzyl wherein the substituent is selected from $C_{1-6}$ alkyl, $NO_2$ and halo; phenyl and substituted phenyl wherein the substituent is selected from $C_{1-6}$ alkyl, $NO_2$, $C_{1-6}$ alkoxy and halo;

$R_2$ and $R_3$ are the same or different and are selected from $CO_2H$, $CO_2C_{1-6}$ alkyl, CN, $CONH_2$, $CON(R_4)_2$ wherein $R_4$ is $C_{1-6}$ alkyl; 5-tetrazolo, CONHOH and $CONR_4OH$, wherein $R_4$ is $C_{1-6}$ alkyl; $CONHR_4$ wherein $R_4$ is 5-tetrazolo and X is selected from S, SO and $SO_2$.

2. The compound of claim 1 wherein $R_1$ is $C_{1-10}$ alkyl; $R_2$ is COOH or 5-tetrazolo and $R_3$ is COOH, CN or $COOC_{1-6}$ alkyl.

3. The compound of claim 1 wherein X is S.
4. The compound of claim 1 wherein X is SO.
5. The compound of claim 1 wherein X is $SO_2$.
6. The compound of claim 1 selected from the group consisting of disodium 5-butyl-1,3-bis[4-(2'-carboxyphenyl)benzyl]mercapto-1,2,4-triazole; 5-pentyl-1,3-bis[4-(2'-carboxyphenyl)benzyl]mercapto-1,2,4-triazole; 3-[4-(2'-carbomethoxyphenyl)benzyl]mercapto-5-pentyl-1-[4-(2'-tetrazolophenyl)benzyl]-1,2,4-triazole; 3-[4-(2'-cyanophenyl)benzyl]mercapto-5-pentyl-1-[4-(2'-tetrazolophenyl)benzyl]-1,2,4-triazole; and 1-[(2'-carboxyphenyl)benzyl]-3-[(2'-carboxyphenyl)benzylsulfonyl]-5-heptyl-1,2,4-triazole.

7. A pharmaceutical composition comprising an effective amount of a compound of claim 1 as the active ingredient dispersed in a pharmaceutically acceptable carrier.

8. A method of treating a physiological condition in a mammal that is mediated by angiotensin II which comprises administering to said mammal an effective amount of a compound of claim 1.

* * * * *